US009049884B2

(12) United States Patent
Barrett-Reis

(10) Patent No.: US 9,049,884 B2
(45) Date of Patent: Jun. 9, 2015

(54) METHODS OF MODULATING INFLAMMATION IN PRETERM INFANTS USING CAROTENOIDS

(75) Inventor: Bridget Barrett-Reis, Dublin, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 204 days.

(21) Appl. No.: 12/950,989

(22) Filed: Nov. 19, 2010

(65) Prior Publication Data

US 2011/0136734 A1 Jun. 9, 2011

Related U.S. Application Data

(60) Provisional application No. 61/266,717, filed on Dec. 4, 2009.

(51) Int. Cl.
| | | |
|---|---|---|
| *A23L 1/303* | (2006.01) | |
| *A23L 1/29* | (2006.01) | |
| *A23L 1/30* | (2006.01) | |
| *A61K 31/015* | (2006.01) | |
| *A61K 31/065* | (2006.01) | |
| *A61K 31/20* | (2006.01) | |
| *A61K 31/70* | (2006.01) | |
| *A61K 45/06* | (2006.01) | |

(52) U.S. Cl.
CPC .................. *A23L 1/303* (2013.01); *A23L 1/296* (2013.01); *A23L 1/3002* (2013.01); *A23V 2002/00* (2013.01); *A61K 31/015* (2013.01); *A61K 31/065* (2013.01); *A61K 31/20* (2013.01); *A61K 31/70* (2013.01); *A61K 45/06* (2013.01)

(58) Field of Classification Search
CPC .................................................. A23V 2002/00
See application file for complete search history.

(56) References Cited

U.S. PATENT DOCUMENTS

| | | | | |
|---|---|---|---|---|
| 4,871,768 | A | | 10/1989 | Bistrian et al. |
| 5,886,053 | A | * | 3/1999 | Schmutzler et al. .......... 514/763 |
| 6,160,007 | A | | 12/2000 | DeMichele et al. |
| 6,306,908 | B1 | | 10/2001 | Carlson et al. |
| 6,316,012 | B1 | | 11/2001 | Nguyen |
| 6,344,214 | B1 | | 2/2002 | Lorenz |
| 6,354,218 | B1 | | 3/2002 | Weise et al. |
| 6,365,218 | B1 | | 4/2002 | Borschel et al. |
| 6,579,543 | B1 | | 6/2003 | McClung |
| 6,589,576 | B2 | | 7/2003 | Borschel et al. |
| 6,645,510 | B1 | | 11/2003 | Coury et al. |
| 7,090,879 | B2 | | 8/2006 | Albrecht et al. |
| 2003/0118703 | A1 | | 6/2003 | Nguyen et al. |
| 2004/0115309 | A1 | | 6/2004 | Harris |
| 2004/0180102 | A1 | | 9/2004 | Patt |
| 2005/0058672 | A1 | | 3/2005 | Gupta |
| 2005/0208179 | A1 | | 9/2005 | Albrecht et al. |
| 2006/0039954 | A1 | | 2/2006 | Gierhart et al. |
| 2006/0058269 | A1 | | 3/2006 | Lockwood et al. |
| 2006/0089411 | A1 | | 4/2006 | Gierhart |
| 2006/0106116 | A1 | | 5/2006 | Fujii et al. |
| 2006/0127505 | A1 | | 6/2006 | Haines et al. |
| 2006/0185034 | A1 | * | 8/2006 | Todd et al. ..................... 800/282 |
| 2006/0270590 | A1 | | 11/2006 | Lockwood et al. |
| 2007/0053849 | A1 | | 3/2007 | Doyle et al. |
| 2007/0078180 | A1 | | 4/2007 | Kern et al. |
| 2007/0166354 | A1 | * | 7/2007 | Barrett-Reis ................. 424/439 |
| 2007/0190080 | A1 | | 8/2007 | Friedman |
| 2007/0207116 | A1 | | 9/2007 | Brown |
| 2008/0063607 | A1 | | 3/2008 | Tamarkin et al. |
| 2008/0176956 | A1 | | 7/2008 | Hsu |
| 2008/0260677 | A1 | | 10/2008 | Pandya |
| 2008/0260924 | A1 | | 10/2008 | Chen et al. |
| 2009/0018186 | A1 | | 1/2009 | Chen et al. |
| 2009/0118227 | A1 | | 5/2009 | Jouni et al. |
| 2009/0118228 | A1 | | 5/2009 | Jouni et al. |

FOREIGN PATENT DOCUMENTS

| | | |
|---|---|---|
| DE | 20202562 U1 | 6/2002 |
| DE | 20310493 U1 | 11/2003 |
| DE | 202004013288 U1 | 12/2004 |
| DE | 202007007584 U1 | 9/2007 |
| DE | 202008009883 U1 | 1/2009 |
| JP | 2008074717 | 4/2008 |
| WO | 9500130 A1 | 1/1995 |
| WO | 2004069186 A2 | 8/2004 |
| WO | 2004112776 A2 | 12/2004 |
| WO | 2005087208 A2 | 9/2005 |
| WO | 2006060578 A2 | 6/2006 |
| WO | 2008006581 A2 | 1/2008 |
| WO | 2008028635 A1 | 3/2008 |
| WO | 2008046857 A1 | 4/2008 |

(Continued)

OTHER PUBLICATIONS

Ewerbeck et al. Acta Paediatr Hung 1984.*
Gotsch et al. Clinical Obstetrics and Gynecology Sep. 2007.*
Daniels et al. PostScript 2004.*
La Hood et al. American Family Physician 2007.*
Bettler, et al., "Serum Lutein Concentions in Healthy Term Infants Fed Human Milk or Infant Formula With Lutein," Eur. J. Nutr. (2009).
Cser, et al., "Serum Carotenoid and Retinol Levels During Childhood Infections," Ann. Nutr. Metabl. 48.3 9, pp. 156-162 (2004).
Ostrea et al., "Influence of Breast-Feeding on the Restoration of the Low Serum Concentration of Vitamin E and Beta-carotene in the Newborn Infant," Am J Obstet Gynecol, vol. 154, pp. 1014-1017 (1986).
Neuringer et al., "Visual Development: Neural Basis and New Assessment Methods," J. Pediatr, vol. 143, pp. S87-S95 (2003).

(Continued)

*Primary Examiner* — James H Alstrum Acevedo
*Assistant Examiner* — Li Lee
(74) *Attorney, Agent, or Firm* — Calfee, Halter & Griswold LLP

(57) ABSTRACT

The present disclosure relates to preterm infant formulas comprising lutein, lycopene, and beta-carotene, and the use of the preterm infant formulas to modulate inflammation, such as skin inflammation, in preterm infants. Also disclosed are methods of modulating the level of C-reactive protein in a preterm infant using preterm infant formulas comprising mixtures of carotenoids.

21 Claims, 4 Drawing Sheets

(56) References Cited

FOREIGN PATENT DOCUMENTS

| WO | 2008046865 A2 | 4/2008 |
|---|---|---|
| WO | 2009007975 A1 | 1/2009 |

OTHER PUBLICATIONS

Hylander et al., "Association of Human Milk Feeding with a Reduction in Retinopathy of Prematurity Among Very Low Birthweight Infants," J. Perinator, vol. 21, pp. 356-362 (2001).
Jewel et al., A Comparison of Lutein and Zeaxanthin Concentrations in Formula and Human Milk Samples from Northern Ireland Mothers, Eur J Clin Nutr, vol. 58, pp. 90-97 (2004).
Tamai et al., "Fat-Soluble Vitamins in Cord Blood and Colostrum in the South of China," Int J Vitamin Nutr Res, vol. 66, pp. 222-226 (1996).
Hack et al., "Very Low Birth Weight Outcomes of the National Institute of Child Health and Human Development Neonatal Network", Pediatrics, vol. 87, pp. 587-597 (1991).
Curran-Celentano et al., "Relation Between Dietary Intake, Serum Concentrations, and Retinal Concentrations of Lutein and Zeaxanthin in Adults in a Midwest Population," Am J Clin Nutr, vol. 74, pp. 796-802 (2001).
Kim et al., "Vitamin A and Carotenoids in Human Milk," J. Agric. Food Chem., vol. 38, pp. 1930-1933 (1990).
Chucair AJ, Rotstein NP and SanGrovanni JP et al., "Lutein and Zeaxanthin Protect Photoreceptors from Apoptosis Induced by Oxidative Stress: Relation with Docosahexaenoic Acid," Invest Ophthalmol Vis Sci., vol. 48, pp. 5168-5177 (2007).
An International Classification of Retinopathy of Prematurity. "The Committee for the Classification of Retinopathy of Prematurity," Arch Ophthalmol, vol. 102, pp. 1130-1134 (1984).
Bell et al., "Neonatal Necrotizing Enterocolitis. Therapeutic Decisions Based Upon Clinical Staging," Ann Surg, vol. 187, pp. 1-7 (1978).
Caplan et al., "New Concepts in Necrotizing Enterocolitis," Curr Opin Pediatr., vol. 2, pp. 111-1115 (2001).
Ehrenkranz et al., "Growth in the Neonatal Intensive Care Unit Influenced Neurodevelopmental and Growth Outcomes of Extremely Low Birth Weight Infants," Pediatrics, vol. 117, pp. 1253-1261 (2006).
Fulton et al., "Photoreceptor Function in Infants and Children with a History of Mild Retinopathy of Prematurity", J Opt Soc Am, vol. 13, pp. 566-571, (1996).
Yeum, et al., "Relationship of Plasma Carotenoids, Retinol, and Tocopherols in Mothers and Newborn Infants," J Am Coll Nutr, vol. 17, pp. 442-447 (1998).
Uuay, et al., Necrotizing Enterocolitis in Very Low Birth Weight Infants: Biodemographic and Clinical Correlates, J Pediatr, vol. 119, pp. 630-638 (1991).
Stoll et al., "Infectnions in VLBW Infants: Studies from the NICHD Neonatal Research Network," Seminars in Perinatology, vol. 27, No. 4, pp. 293-301 (2003).
Stahl, et al., "Dietary Tomato Paste Protects Against Ultraviolet Light-Induced Erythema in Humans," J Nutr, vol. 131, pp. 1449-1451 (2001).
Ruhl, et al., "Relation of Elevated Serum Alanine Aminotransferase Activity with Iron and Antioxidant Levels in the United States," Gastroenterol, vol. 124, pp. 1821-1829 (2003).
Patole, et al., "Prevention and Treatment of Necrotizing Enterocolitis in Preterm Neonates," Early Human Development Sep. 2007 doi: 10.1016/jearlhumdev.2007.07.007.
Pepys, "The Acute Phase Response and C-Reactive Protein," Oxford Textbook of Medicine, Oxford University Press, pp. 1527-1533 (1996).
Fulton et al., "The development of Scoptic Sensitivity," Invest, Ophthalmol. Vis Sci., vol. 41, pp. 1588-1596 (2000).
Mayer et al., "Validity and Reliability in Studies of Human Visual Development in Dobbing J (eds): Developing Brain and Behavoir," San Diego: Academic Press Ltd., pp. 253-292 (1997).
Neu, "Necrotizing Enterocolitis: The Search for a Unifying Pathogenic Theory Leading to Prevention," Pediatr Clin North Am., vol. 43, pp. 409-432, (1996).
Fulton, et al., "The Rod Photoreceptors in Retinopathy of Prematurity: An Electroretinographic Study," Arch Ophthalmol, vol. 119, pp. 499-505 (2001).
Fulton, et al., "Development of ERG responses: the ISCEV Rod, Maxmal and Cone Responses in Normal Subjects," Doc Ophthal, vol. 107, pp. 235-241 (2003).
Fulton, et al., "Photoreceptor Function in Infants and Children with a History of Mild Retinopathy of Prematurity," J. Opt Soc. Am., vol. 13, pp. 566-571 (1996).
Guillet, et al., "Association of H2-blocker Therapy and Higher Incidence of Necrotizing Enterocolitis in Very Low Birth Weight Infants," Pediatrics, vol. 117, pp. e137-e142 (2003).
Hamilton, et al., "Maturation of Rod Function in Preterm Infants with an without Retinopathy of Prematurity," J. Pediatr, vol. 153(5), pp. 605-611 (2008).
Hylander, et al., "Human Milk Feedings and Infection Among Very Low Birth Weight Infants," Pediatrics, vol. 102, p. e38 (1998).
Infant Formula Act of 1980, Public Law 96-359, Sep. 26, 1980.
Neuringer, et al., "Lutein in Breastmilk and Infant Formula: Effects on Serum Lutein, Macular Pigment and Visual Function," Abstract A287 (2009).
Papile, et al., "Incidence and Evolution of Subependymal and Intraventricular Hemorrhage: A Study of Infants with Birthweights Less Than 1,500 Grams," J. Pediar, vol. 92, pp. 529-534 (1978).
Williams, et al., "Factors Influencing the Uptake and Absorption of Carotenoids," Proc. Soc. Exp. Biol. Med., vol. 218, pp. 106-108 (1998).
Agarwal and Rao, "Carotenoids and Chronic Diseases," Drug Metabol Drug Interact., vol. 17, pp. 189-210 (2000).
Byers and Perry, "Dietary Carotenes, Vitamin C, and Vitamin E as protective Antioxidants in Human Cancers," Annu. Rev. Nutr., vol. 12, pp. 139-159 (1992).
Mares-Perlman, et al., "The Body of Evidence to Support a Protective Role for Lutein and Zeaxanthin in Delaying Chronic Disease," J. Nutr., vol. 132, pp. 518-524 (2002).
Nishino, et al., "Carotenoids in Cancer Chemoprevention," Cancer Meta. Rev., vol. 21, pp. 257-264 (2002).
Gitto, et al., "Oxidative and Inflammatory Parameters in Respiratory Distress Syndrome of Preterm Newborns: Beneficial Effects of Melatonin," Am. J. Perinatol, vol. 21, pp. 209-216 (2004).
Ochoa, et al., "Oxidative Stress in Erythrocytes from Premature and Full-Term Infants during their First 72h of Life," Free Rad. Res. vol. 37, pp. 317-322 (2003).
Saugstad, "Bronchopulmonary Displasia—Oxidative Stress and Antioxidants," Sem. Neonatol., vol. 3, pp. 39-49 (2003).
Macias and Schweigert, "Changes in the Concentration of Carotenoids, Vitamin A, Alpha-Tocopherol and Total Lipids in Human Milk Throughout Early Lactation," Ann Nutr Metab, vol. 45, pp. 82-85 (2001).
Khachik, et al., "Chemistry, Distribution, and Metabolism of Tomato Carotenoids and Their Impact on Human Health," Exp. Bio. Med., vol. 227, pp. 845-851 (2002).
INFORM, Structured Lipids Allow Fat Tailoring, vol. 8, No. 10, p. 1004 (Oct. 1997).
Mackey, et al., "Relative Bioavailability of Carotenoids in Infant Formula and Human Milk," presented at Clinical Nutrition Week, Chicago (Feb. 2008).
American Academy of Pediatrics, Committee on Nutrition: "Commentary on Breast-Feeding and Infant Formulas, Including Proposed Standards for Formulas," Pediatrics, vol. 57, pp. 278-285 (1976).
Chew and Park, "Carotenoid Action on the Immune Response," J Nutr, vol. 134, pp. 257-261S (2004).
Sies and Stahl, "Carotenoids and Intercellular Communication Via Gap Junctions," Int J Vitam Nutr Res., vol. 67, pp. 364-367 (1997).
Stahl et al., "Non-Antioxidant Properties of Carotenoids," Biol Chem, vol. 383, pp. 553-558 (2002).
Stahl and Sies, "Effects of Carotenoids and retinoids on Gap Junctional Communication," Biofactors, vol. 15, pp. 95-98 (2001).
Landrum and Bone, "Lutein, Zeaxanthin, and the Macular Pigment," Arch Biochem Biophys, vol. 385, pp. 28-40 (2001).

(56) References Cited

OTHER PUBLICATIONS

Davies and Morland, "Macular Pigments: Their Characteristics and Putative Role," Prog Retin Eye Res., vol. 23, pp. 533-559 (2004).
Bernstein et al., "Resonance Raman Measurement of Macular Carotenoids in Normal Subjects and in Age-Related Macular Degeneration Patients," Ophthalmology, vol. 109, pp. 1780-1787 (2002).
Bone et al., "Macular Pigment in Donor Eyes with and without AMD: A Case-Control Study," Invest Ophthalmol Vis Sci, vol. 42, pp. 235-240 (2001).
Broekmans et al., "Macular Pigment Density in relation to Serum and Adipose Tissue Concentrations of Lutein and Serum Concentrations of Zeaxanthin," Am J. Clin Nutr, vol. 76, pp. 595-603 (2002).
American Academy of Pediatrics, "Nutritional Needs of the Preterm Infant", Pediatric Nutrition Handbook (5th ed), pp. 23-54 (2004).
Seddon et al., "Dietary Carotenoids, Vitamins A, C, and E, and Advance Age-Related Macular Degeneration," Eye Disease Case-Control Study Group, JAMA, vol. 272, pp. 1413-1420 (1994).
Bone, "Lutein and Zeaxanthin Dietary Supplementa Raise Macular Pigment Density and Serum Concentration of these Carotenoids in Humans," J. Nut., vol. 133, pp. 992-998 (2003).
Hammond et al., "Dietary Modification of Human Macular Pigment Density," Invest Ophthalmol Vis Sci., vol. 38, pp. 1795-1801 (1997).
Johnson, "Relation Among Serum and Tissue Concentrations of Lutein and Zeaxanthin and Macular Pigment Density," Am. J Clin Nutr., vol. 71, pp. 555-562 (2000).
Richer et al., "Double-Masked, Placebo-Controlled, Randomized Trial of Lutein and Antioxidant Supplementation in the Intervention of Atrophic Age-Related Macular Degeneration: the Veterans LAST Study (Lutein Antioxidant Supplementation Trial)," Optometry, vol. 75, pp. 216-230 (2004).
Heinrich et al., "Supplementation with Beta-Carotene or a Similar Amount of Mixed Carotenoids Protects Humans from UV-Induced Erythema," J Nutr., vol. 133, pp. 98-101 (2003).
Lee et al., "Carotenoid Supplementation Reduces Erythema in Human Skin After Simulated Solar Radiation Exposure," Proc Soc Exp Biol Med, vol. 223, pp. 170-174 (2000).
Sommerburg et al., "Carotenoid Supply in Breast-Fed and Formula-Fed Neonates," Eur J Pediatr, vol. 159, pp. 86-90 (2000).
Stahl et al., "Carotenoids and Carotenoids Plus Vitamin E Protect Against Ultraviolet Light-Induced Erythema in Humans", Am J Clin Nutr, vol. 71, pp. 795-798, (2000).
Cooper et al., "Dietary Carotenoids and Certain Cancers, Heart Disease, and Age-Related Macular Degeneration: a Review of Recent Research," Nutr. Rev., vol. 57, pp. 201-214 (1999).
Cooper, "Carotenoids in Health and Disease: Recent Scientific Evaluations, Research Recommendations, and the Consumer," J Nutr, vol. 134, pp. 221-224 (2004).
Erdman, Jr. et al., "Absorption and Transport of Carotenoids," Ann N Y Acad Sci, vol. 691, pp. 76-85 (1993).

Castenmiller et al., "The Food Matrix of Spinach is a Limiting Factor in Determining the Bioavailability of Beta-Carotene and to a Lesser Extent of Lutein in Humans," J Nutr, vol. 129, pp. 349-355 (1999).
Richelle et al., "A Food-Based Formulation Provides Lycopene with the Same Bioavailability to Humans as that from Tomato Paste," J Nutr, vol. 132, pp. 404-408 (2002).
Hoppe et al., "Synthetic and Tomato-Based Lycopene have Identical Bioavailability in Humans," Eur J Nutr, vol. 42, pp. 272-278 (2003).
Minicucci et al., "Abnormal Retinal Vascularization in Preterm Children," Lancet, vol. 353, p. 1099 (1999).
"An International Classification of Retinopathy of Prematurity," Pediatrics, vol. 74, pp. 127-133 (1984).
Herrera et al., "Relationship Between Plasma Fatty Acid Profile and Antioxidant Vitamins During Normal Pregnancy," Eur J Clin Nutr, pp. 1-8 (2004).
Kiely et al., "Concentrations of Tocopherols and Carotenoids in Maternal and Cord Blood Plasma," Eur J Clin Nutr, vol. 53, pp. 711-715 (1999).
Yeum et al., "Human Plasma Carotenoid Response to the Ingestion of Controlled Diets High in Fruits and Vegetables," Am. J. Clin. Nutr., vol. 63, pp. 594-602 (1996).
Infant Formula Act Amendments, 21 Code of Federal Regulations (As Amended), [412], Sec. 350a, Infant Formulas, (Oct. 27, 1986).
Canfield et al., "Multinational Study of Major Breast Milk Carotenoids of Healthy Mothers," Eur J Nutr, vol. 42, pp. 133-141 (2003).
Canfield et al., "Beta-Carotene in Breast Milk and Serum is Increased After a Single Beta-Carotene Dose," Am J Clin Nutr, vol. 66, No. 3, pp. 52-61 (1997).
Canfield et al., "Kinetics of the Response of Milk and Serum ↑-Carotene to Daily Beta-Carotene Supplementation in Healthy, Lactating Women," Am J Clin Nutr, vol. 67, pp. 276-283 (1998).
Canfield et al., "Red Palm Oil in the Maternal Diet Increases Provitamin A Carotenoids in Breastmilk and Serum of the Mother-Infant Dyad," Eur J Nutr, vol. 40, pp. 30-38, (2001).
Gossage et al., "Carotenoid Composition of Human Milk During the First Month Postpartum and the Response to Beta-Carotene Supplementation", Am J Clin Nutr, vol. 76, No. 1, pp. 193-197, (2002).
Khachik et al., "Identification, Quantification, and Relative Concentrations of Carotenoids and Their Metabolites in Human Milk and Serum", Anal Chem, vol. 69, No. 10, pp. 1873-1881, (1997).
International Search Report and Written Opinion from PCT/US2010/057551, dated Sep. 26, 2011.
Seddon, et al., "Association between C-reactive protein and lutein/zeaxanthin, fish intake, body mass index and other age-related macular degeneration risk factors," Annual Meeting of the Association for Research in Vision and Ophthaolmology, abstract, 2005, XP-002658719.
Watzl, et al., "A 4-wk intervention with high intake of carotenoid-rich vegetables and fruit reduces plasma C-reactive protein in healthy, nonsmoking men," American Journal of Clinical Nutrition, vol. 82, No. 5, 2005, p. 1052-1058.

* cited by examiner

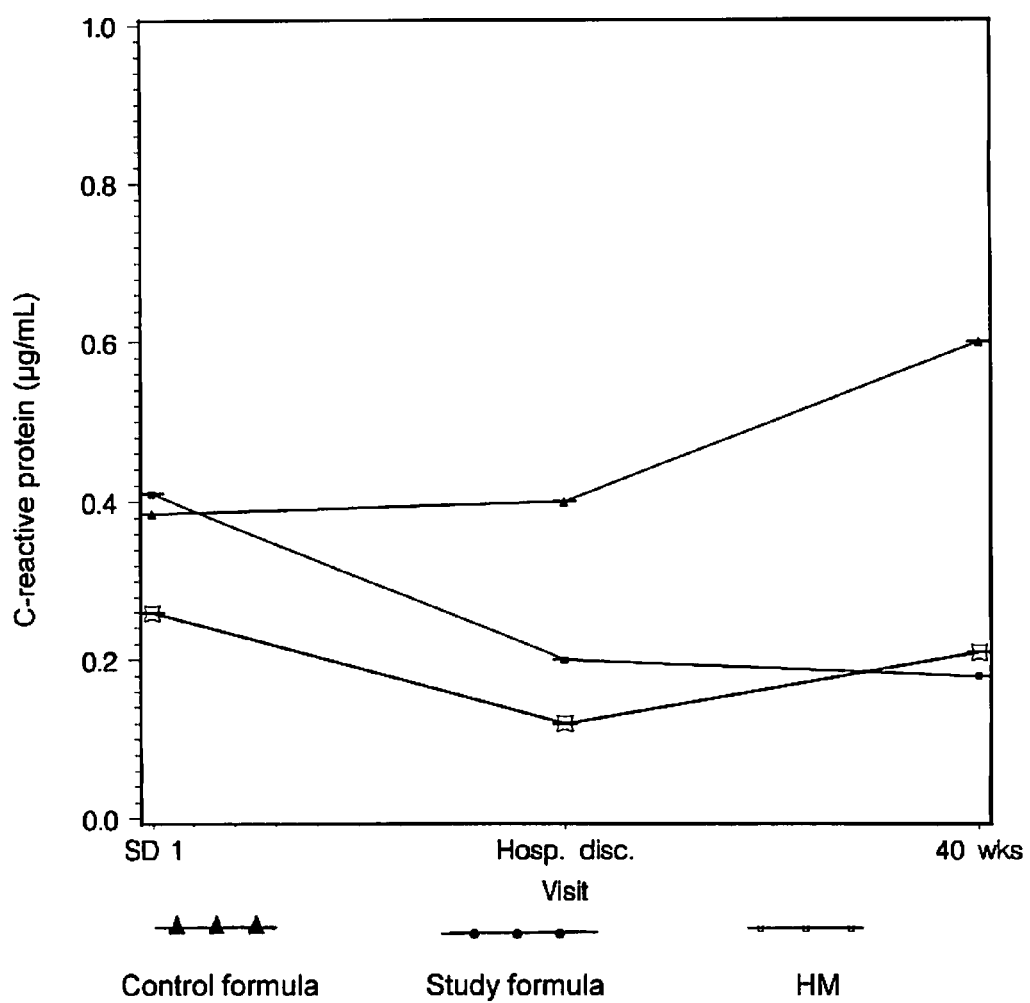
Figure 1 - The median plasma concentration of C-reactive protein at study day (SD) 1, hospital discharge, and 40 weeks PMA for infants Figure 2 - The relationship between the plasma concentration of C-reactive protein and the plasma concentration of lutein for evaluable infants
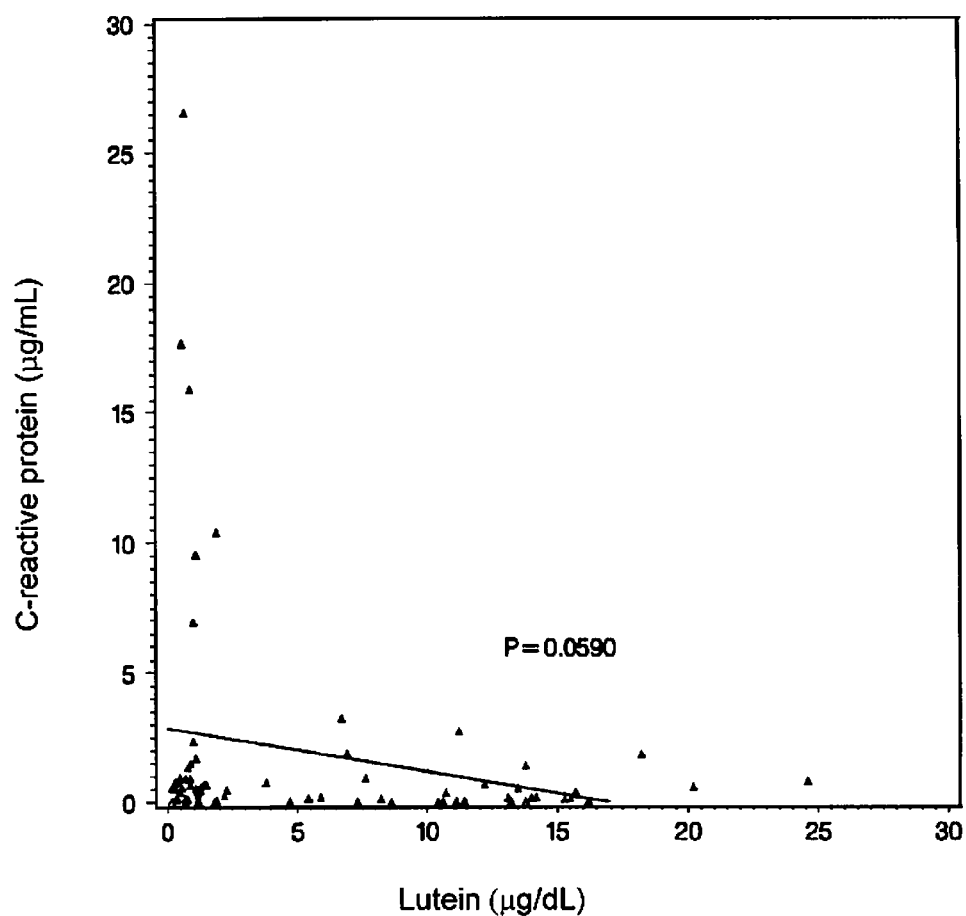

Figure 3 - The relationship between the plasma concentration of C-reactive protein and the plasma concentration of lycopene for evaluable infants
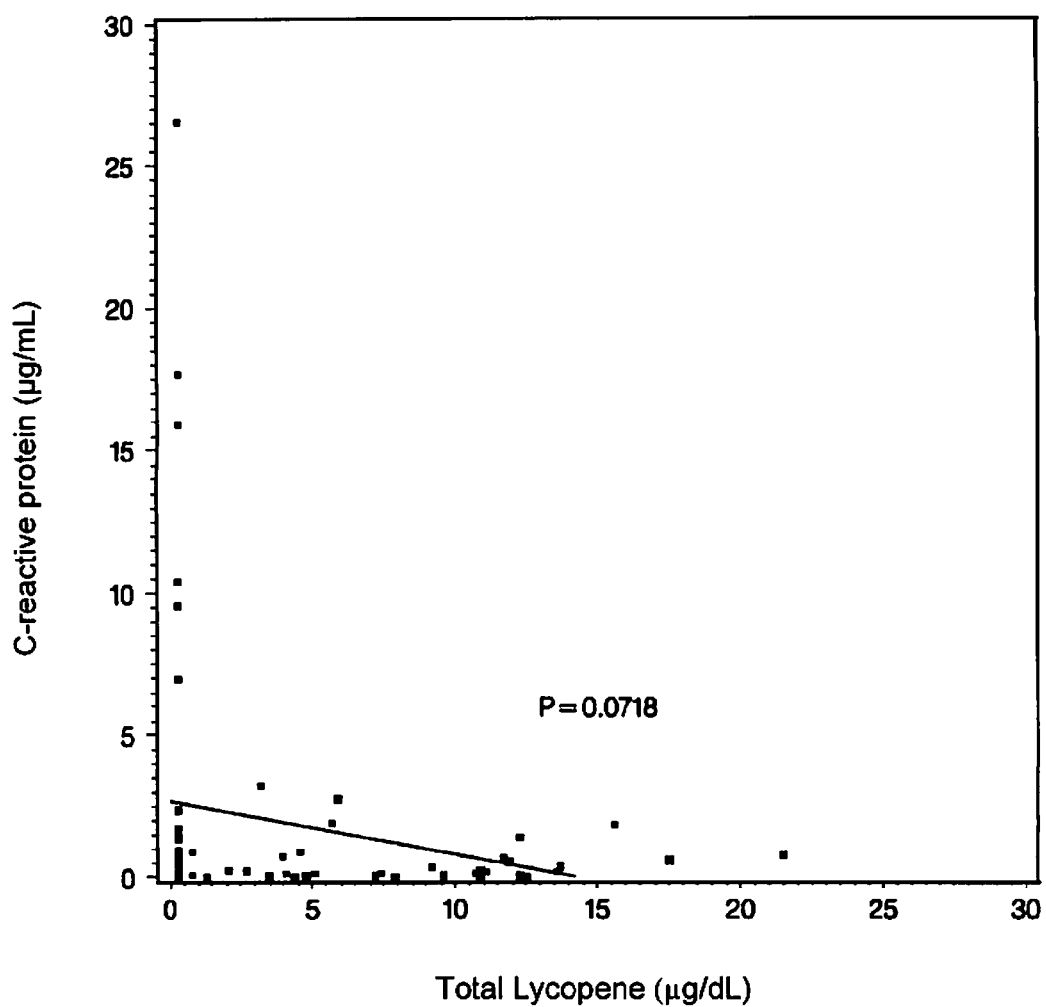

Figure 4 - The relationship between the plasma concentration of C-reactive protein and the plasma concentration of beta carotene for evaluable infants
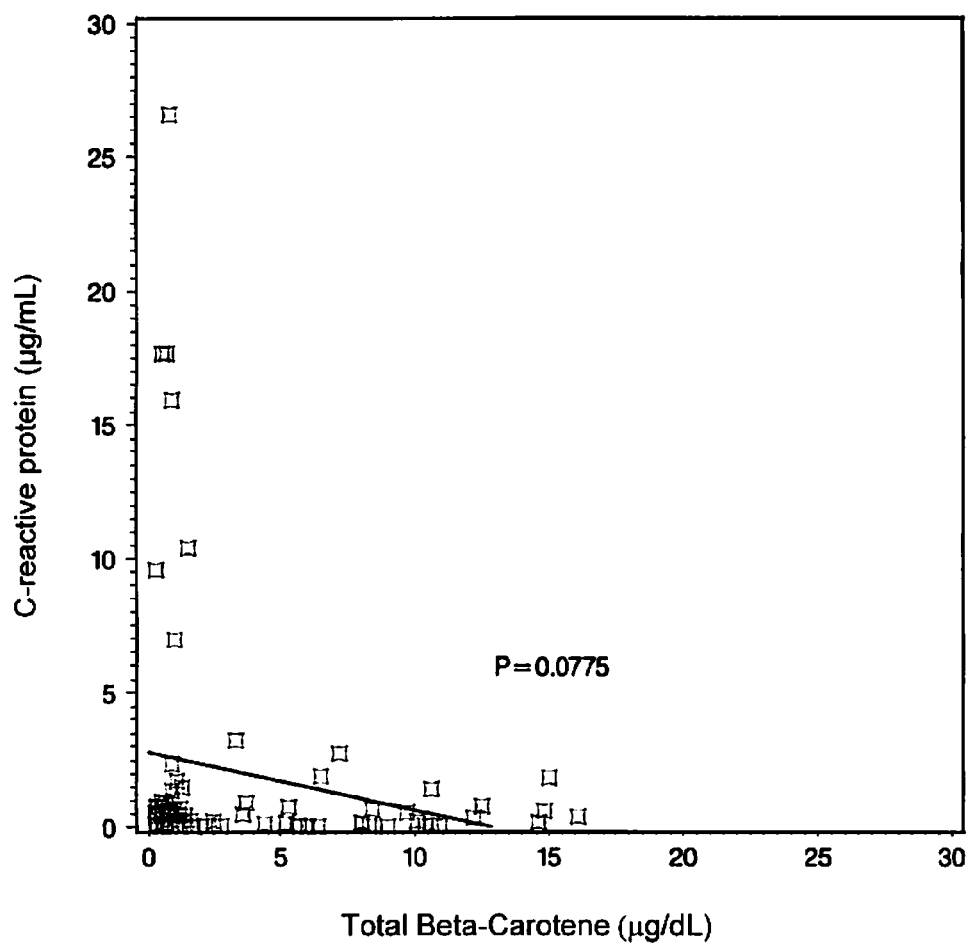

METHODS OF MODULATING INFLAMMATION IN PRETERM INFANTS USING CAROTENOIDS

This application claims the benefit of U.S. Provisional Application No. 61/266,717 filed Dec. 4, 2009

TECHNICAL FIELD

The present disclosure relates to preterm infant formulas comprising lutein, lycopene, and beta-carotene, and the use of the preterm infant formulas to modulate inflammation, such as skin inflammation, in preterm infants.

BACKGROUND OF THE DISCLOSURE

Dietary carotenoids are lipid soluble compounds abundant in fruits and vegetables. Carotenoids are responsible the spectrum of color found in fruits and vegetables, and are also responsible for the coloring of some birds and shellfish. Hundreds of carotenoid compounds have been identified, and approximately 30 of these compounds have been detected in human serum, milk, and other tissues (Khachik, et al., "Chemistry, distribution, and metabolism of tomato carotenoids and their impact on human health," *Exp. Biol. Med.* 2002, Vol. 227:845-851).

Human milk provides a variety of antioxidants to the breastfed infant. In contrast, exclusively formula-fed infants do not receive the variety or the quantity of carotenoids that are ingested by breastfed infants until other complementary foods are introduced to the diet. The lack of carotenoids in the diets of formula fed infants may be particularly problematic in preterm infants.

Infants who are born prior to 37 weeks gestation often face complications resulting from their prematurity. For instance, preterm infants are more susceptible to increased morbidities that are not common in healthy term infants. Underdeveloped organs such as the lungs, eye, intestines, and brain can reveal conditions such as chronic lung disease, bronchopulmonary dysplasia (BPD), retinopathy of prematurity (ROP), necrotizing enterocolitis (NEC), and intraventricular hemorrhage (IVH). Infants in the NICU often have increased inflammation and oxidative stress associated with common diseases of prematurity as well as the treatments used to combat these illnesses (Gitto, et al., *Am. J. Perinatal.* 2004, Vol. 21:209-216; Ochoa, et al., *Free Rad. Res.* 2003, Vol. 37:317-322; Saugstad, *Sem. Neonatal.* 2003, Vol. 3:39-49).

Preterm infants are also at a nutritional disadvantage at birth, as they have been deprived of the period of maximal transfer of nutrients during the last few weeks of pregnancy. Consequently, it would therefore be desirable to provide a preterm infant formula comprising sufficient levels of carotenoids, such as lutein, lycopene, and beta-carotene, to modulate inflammation in preterm infants, such as inflammation associated with common diseases of prematurity.

It has now been unexpectedly discovered that inflammation in preterm infants, particularly skin inflammation, can be modulated by administering to the preterm infant a preterm infant formula that has been supplemented with a mixture of lutein, lycopene, and beta-carotene. More particularly, it has been discovered that preterm infant formulas containing certain levels of beta-carotene, lutein, and lycopene, can be used to decrease plasma levels of the inflammation marker C-reactive protein, and consequently decrease inflammation in preterm infants.

SUMMARY OF THE DISCLOSURE

The present disclosure is directed to a method for modulating inflammation in preterm infants. The method comprises administering to the preterm infant a preterm infant formula comprising from about 75 μg/L to about 500 μg/L of lutein, from about 60 μg/L to about 500 μg/L of lycopene, and from about 85 μg/L to about 500 μg/L of beta-carotene.

In another aspect, the present disclosure is directed to a method for modulating levels of C-reactive protein in preterm infants. The method comprises administering to the preterm infant a preterm infant formula comprising from about 75 μg/L to about 500 μg/L of lutein, from about 60 μg/L to about 500 μg/L of lycopene, and from about 85 μg/L to about 500 μg/L of beta-carotene.

It has been discovered that administering a preterm infant formula containing certain levels of carotenoids, such as beta-carotene, lutein, and lycopene, to a preterm infant results in a decrease in the plasma concentration of C-reactive protein in the preterm infant. Since C-reactive protein is a well known marker for inflammatory conditions, by decreasing plasma concentrations of C-reactive protein in the preterm infant, the level of inflammation can also be modulated.

BRIEF DESCRIPTION OF THE DRAWINGS

FIG. 1 is a graph showing the median plasma concentration of C-reactive protein at study day (SD) 1, hospital discharge, and 40 weeks PMA for infants in the control formula group (no added carotenoids), infants in the study formula group (added carotenoids), and infants in the human milk (HM) fed reference group, as discussed in Example 16.

FIG. 2 is a graph showing the relationship between the plasma concentration of C-reactive protein and the plasma concentration of lutein for evaluable infants in the study formula group (added carotenoids), as discussed in Example 16. Plasma concentration of lutein was inversely related to plasma concentration of C-reactive protein.

FIG. 3 is a graph showing the relationship between the plasma concentration of C-reactive protein and the plasma concentration of lycopene for evaluable infants in the study formula group (added carotenoids), as discussed in Example 16. Plasma concentration of lycopene was inversely related to plasma concentration of C-reactive protein.

FIG. 4 is a graph showing the relationship between the plasma concentration of C-reactive protein and the plasma concentration of beta-carotene for evaluable infants in the study formula group (added carotenoids), as discussed in Example 16. Plasma concentration of beta-carotene was inversely related to plasma concentration of C-reactive protein.

DETAILED DESCRIPTION OF THE DISCLOSURE

The present disclosure is directed to methods for modulating levels of C-reactive protein, and consequently inflammation, in preterm infants using a preterm infant formula comprising a select level of the carotenoids beta-carotene, lutein, and lycopene. More particularly, it has been discovered that when preterm infant formulas containing select levels of the carotenoids beta-carotene, lutein, and lycopene are administered to preterm infants, the plasma concentration of C-reactive protein in the infants is decreased. By decreasing plasma concentrations of C-reactive protein, the level of inflammation in preterm infants can be modulated. These and other essential or optional elements or limitations of the preterm infant formulas and methods of the present disclosure are described in detail hereafter.

The term "infant" as used herein, unless otherwise specified, refers to children not more than about one year of age, and includes infants from 0 to about 4 months of age, infants from about 4 to about 8 months of age, infants from about 8 to about 12 months of age, low birth weight infants at less than 2,500 grams at birth, and preterm infants.

The terms "preterm infant" or "premature infant," used interchangeably herein, unless otherwise specified, refer to infants born at less than about 37 weeks gestational age, typically from about 26 weeks to about 34 weeks gestational age. A "term" infant is an infant born at about 37 to about 42 weeks gestational age. While actual conception, and thus gestational age, may not be precisely determinable, it can be approximated based on last menstrual cycle and/or on other objective estimates, such as early ultrasound assessments or clinical neonatal assessments such as Ballard's. The choice of which method to use in the event of discrepant results is often a matter of physician or institution preference.

The term "corrected age" (CA) refers to a concept used to standardize preterm infants to their full term peers for purposes of comparing their growth and development. Corrected age represents the age of the child from the expected date of delivery. Corrected age is calculated by subtracting the number of weeks born before 40 weeks of gestation from the chronological age. For example, a preterm infant born 8 weeks prematurely reaches "term corrected age" at approximately 2 months chronological age, and at 6 months chronological age may developmentally be equivalent to a 4 month-old term infant.

The term "chronological age" (or "postnatal" age) is the time elapsed after birth (gestational age).

The term "post-menstrual age" (PMA) refers to the time elapsed between the first day of the last menstrual period and birth (gestational age) plus the time elapsed after birth (chronological age).

The term "preterm infant formula" as used herein, unless otherwise specified, refers to a nutritional formula designed for preterm infants that contains sufficient nutrients such as proteins, carbohydrates, lipids, vitamins, and minerals to potentially serve as a supplemental, primary, or sole source of nutrition.

The term "nutritional formula" as used herein, unless otherwise specified, refers to a nutritional composition designed for infants, toddlers, children, adults, or combinations thereof, that contains sufficient nutrients such as proteins, carbohydrates, lipids, vitamins, minerals, and electrolytes to potentially serve as a supplemental, primary, or sole source of nutrition.

The term "ready-to-feed" as used herein, unless otherwise specified, refers to nutritional formulas in liquid form suitable for administration, including reconstituted powders, diluted concentrates, and manufactured liquids.

All percentages, parts and ratios as used herein, are by weight of the total formula, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The preterm infant formulas of the present disclosure may also be substantially free of any optional or selected essential ingredient or feature described herein, provided that the remaining formula still contains all of the required ingredients or features as described herein. In this context, and unless otherwise specified, the term "substantially free" means that the selected formula contains less than a functional amount of the optional ingredient, typically less than 0.1% by weight, and also including zero percent by weight of such optional or selected essential ingredient.

The preterm infant formulas and corresponding methods of use of the present disclosure can comprise, consist of, or consist essentially of the essential elements and limitations of the disclosure as described herein, as well as any additional or optional ingredients, components, or limitations described herein or otherwise useful in nutritional formula applications.

Carotenoids

The preterm infant formulas of the present disclosure comprise select combinations of the carotenoids lutein, lycopene, and beta-carotene. Preterm infant formulas containing these combinations, as selected and defined herein, can be used to modulate inflammation and/or levels of C-reactive protein in preterm infants.

It is generally preferable that the preterm infant formula comprise from about 75 µg/L to about 500 µg/L of lutein, including from about 100 µg/L to about 350 µg/L of lutein, and also including from about 200 µg/L to about 250 µg/L of lutein and from about 100 µg/L to about 215 µg/L of lutein. It is also generally preferable that preterm infant formula comprise from about 60 µg/L to about 500 µg/L of lycopene, including from about 90 µg/L to about 350 µg/L of lycopene, and also including from about 100 µg/L to about 150 µg/L of lycopene. It is also generally preferable that preterm infant formula comprise from about 85 µg/L to about 500 µg/L of beta-carotene, including from about 150 µg/L to about 350 µg/L of beta-carotene, and also including from about 200 µg/L to about 250 µg/L of beta-carotene and from about 150 µg/L to about 200 µg/L of beta-carotene. It should be understood that any combination of these amounts of beta-carotene, lutein, and lycopene can be included in the preterm infant formulas of the present disclosure. In one exemplary embodiment, the preterm infant formula of the present disclosure comprises about 211 µg/L of lutein, about 143 µg/L of lycopene, and about 219 µg/L of beta-carotene. In another exemplary embodiment, the preterm infant formula of the present disclosure comprises about 120 µg/L of lutein, about 100 µg/L of lycopene, and about 180 µg/L of beta-carotene. Other carotenoids may optionally be included in the preterm infant formulas as described herein. Any one or all of the carotenoids included in the preterm infant formulas described herein may be from a natural source, or artificially synthesized.

In one embodiment, the preterm infant formula may optionally further comprise the carotenoid zeaxanthin. The preterm infant formulas of the present disclosure may comprise zeaxanthin in amounts of from about 5 µg/L to about 300 µg/L, including from about 10 µg/L to about 100 µg/L or from about 5 µg/L to about 50 µg/L. As will be recognized by one skilled in the art based on the disclosure herein, if lutein is utilized from a naturally-occurring source, some zeaxanthin may also be included in the carotenoids.

Typically, the preterm infant formulas of the present disclosure will comprise lutein, lycopene, and beta-carotene in amounts sufficient to provide from about 22 µg/kg/day to about 150 µg/kg/day of lutein; from about 18 µg/kg/day to about 150 µg/kg/day of lycopene; and from about 26 µg/kg/day to about 150 µg/kg/day of beta-carotene. Optionally, the preterm infant formula may further comprise zeaxanthin in amounts sufficient to provide from about 1 µg/kg/day to about 15 µg/kg/day.

Each of the carotenoids in the selected combinations can be obtained from any known or otherwise suitable material source for use in nutritional formulas, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LycoVit® lycopene (available from BASF, Mount Olive, N.J.), Lyc-O-Mato® tomato extract in oil, powder, or bead form (available from LycoRed Corp., Orange, N.J.), beta-carotene, lutein, or lycopene available from DSM Nutritional Products, Parsippany, N.J.), FloraGLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J.).

Plasma carotenoid concentration can be measured using any suitable technique. For instance, plasma carotenoid concentration can be measured by subjecting a blood sample to high performance liquid chromatography (HPLC). Carotenoid concentration in the skin can be measured using any suitable technique, such as Raman spectroscopy. Raman spectroscopy involves exposing the skin to a laser light source and detecting the scattered light as a function of photon frequency.

Nutrients

The preterm infant formulas of the present disclosure can be incorporated into any food or beverage that can be consumed by human infants, particularly preterm infants, or adults or animals. Thus, in one aspect, the present disclosure is directed to a preterm infant formula. The preterm infant formulas of the present disclosure may comprise sufficient types and amounts of nutrients to meet the targeted dietary needs of the intended user. These preterm infant formulas may therefore comprise protein, carbohydrate, and a lipid component (all either organic or non-organic) in addition to the carotenoids discussed above. The preterm infant formulas may also include vitamins, minerals, or other ingredients suitable for use in preterm infant formulas.

For example, the preterm infant formula includes those embodiments in which the protein component may comprise from about 7.5% to about 25% of the caloric content of the formula; the carbohydrate component may comprise from about 35% to about 50% of the total caloric content of the formula; and the lipid component may comprise from about 30% to about 60% of the total caloric content of the formula. These ranges are provided as examples only, and are not intended to be limiting. Additional suitable ranges are noted in the following Table.

| Nutrient* | 1st Embodiment | 2nd Embodiment | 3rd Embodiment |
|---|---|---|---|
| Carbohydrates: % total calories | 20-85 | 30-60 | 35-55 |
| Lipid: % total calories | 5-70 | 20-60 | 25-50 |
| Protein: % total calories | 2-75 | 5-50 | 7-40 |

*all numerical values preceded by the term "about"

Many different sources and types of carbohydrates, lipids, proteins, minerals and vitamins are known and can be used in the preterm infant formulas of the present disclosure, provided that such nutrients are compatible with the added ingredients in the selected formula, are safe for their intended use, and do not otherwise unduly impair product performance.

Carbohydrates suitable for use in the preterm infant formulas of the present disclosure can be simple, complex, or variations or combinations thereof. Non-limiting examples of suitable carbohydrates include hydrolyzed, intact, naturally and/or chemically modified cornstarch, maltodextrin, glucose polymers, sucrose, corn syrup, corn syrup solids, rice or potato derived carbohydrate, glucose, fructose, lactose, high fructose corn syrup and indigestible oligosaccharides such as fructooligosaccharides (FOS), and combinations thereof.

Non-limiting examples of proteins suitable for use in the preterm infant formulas include extensively hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof. The proteins for use herein can also include, or be entirely or partially replaced by, free amino acids known for use in infant formulas, non-limiting examples of which include tryptophan, glutamine, tyrosine, methionine, cysteine, arginine, and combinations thereof. Other (non-protein) amino acids typically added to infant formulas include carnitine and taurine. In some cases, the D-forms of the amino acids are considered as nutritionally equivalent to the L-forms, and isomer mixtures are used to lower cost (for example, D,L-methionine).

Non-limiting examples of lipids suitable for use in the preterm infant formulas include coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, long-chain polyunsaturated fatty acids such as arachidonic acid (ARA), docosahexaenoic acid (DHA), and eicosapentaenoic acid (EPA), and combinations thereof.

In addition to these food grade oils, structured lipids may be incorporated into the preterm infant formulas if desired. Structured lipids are known in the art, descriptions of which can be found in INFORM, Vol. 8, no. 10, page 1004, Structured lipids allow fat tailoring (October 1997). Structured lipids are predominantly triacylglycerols containing mixtures of medium and long chain fatty acids on the same glycerol nucleus. Structured lipids are also described in U.S. Pat. No. 6,160,007, which is also incorporated herein by reference.

The preterm infant formulas of the present disclosure may further comprise any of a variety of vitamins in addition to the components described above. Non-limiting examples of vitamins include vitamin A, vitamin D, vitamin E, vitamin K, thiamine, riboflavin, pyridoxine, vitamin B12, niacin, folic acid, pantothenic acid, biotin, vitamin C, choline, chromium, carnitine, inositol, salts and derivatives thereof, and combinations thereof.

The preterm infant formulas may further comprise any of a variety of minerals, non-limiting examples of which include calcium, phosphorus, magnesium, iron, zinc, manganese, copper, iodine, sodium, potassium, chloride, and combinations thereof.

The preterm infant formulas of the present disclosure preferably comprise nutrients in accordance with the relevant infant formula guidelines for the targeted consumer or user population, as example of which would be the Infant Formula Act, 21 U.S.C. Section 350(a).

The preterm infant formulas of the present disclosure include those embodiments containing the carbohydrate, lipid, and protein concentrations described in Table 1 (Nutritional Formula Macronutrients).

TABLE 1*

| Nutrient | Embodiment | g/100 kcal | g/100 g total solids | g/L (as fed) |
|---|---|---|---|---|
| Carbohydrate | 1st Embodiment | 8-16 | 30-83 | 54-108 |
| | 2nd Embodiment | 9-13 | 45-60 | 57-79 |
| | 3rd Embodiment | 15-19 | 63-81 | 157-203 |
| Lipid | 1st Embodiment | 3-8 | 15-42 | 20-54 |
| | 2nd Embodiment | 4-6.6 | 20-30 | 27-45 |
| | 3rd Embodiment | 2-5 | 8-21 | 20-53 |
| Protein | 1st Embodiment | 1-3.9 | 5-20.5 | 7-24 |
| | 2nd Embodiment | 1.5-3.4 | 10-17 | 10-23 |
| | 3rd Embodiment | 3.5-6.0 | 14.8-25.3 | 37-63 |

*all numerical values preceded by the term "about"

The preterm infant formulas of the present disclosure include those embodiments that comprise per 100 kcal of reconstituted formula one or more of the following: vitamin A (from about 250 to about 1250 IU), vitamin D (from about 40 to about 150 IU), vitamin K (greater than about 4 mcg), vitamin E (at least about 0.3 IU), vitamin C (at least about 8 mg), thiamine (at least about 8 mcg), vitamin B12 (at least about 0.15 mcg), niacin (at least about 250 mcg), folic acid (at least about 4 mcg), pantothenic acid (at least about 300 mcg), biotin (at least about 1.5 mcg), choline (at least about 7 mg), and inositol (at least about 4 mg).

The preterm infant formulas of the present disclosure include those embodiments that comprise per 100 kcal of reconstituted formula one or more of the following: calcium (at least about 50 mg), phosphorus (at least about 25 mg), magnesium (at least about 6 mg), iron (at least about 0.15 mg), iodine (at least about 5 mcg), zinc (at least about 0.5 mg), copper (at least about 60 mcg), manganese (at least about 5 mcg), sodium (from about 20 to about 60 mg), potassium (from about 80 to about 200 mg), and chloride (from about 55 to about 150 mg).

Optional Ingredients

The preterm infant formulas of the present disclosure may further comprise other optional components that may modify the physical, chemical, aesthetic or processing characteristics of the formulas or serve as pharmaceutical or additional nutritional components when used in the targeted population. Many such optional ingredients are known or other suitable for use in food and nutritional products, including infant formulas, and may also be used in the preterm infant formulas of the present disclosure, provided that such optional materials are compatible with the essential materials described herein, are safe for their intended use, and do not otherwise unduly impair product performance.

Non-limiting examples of such optional ingredients include preservatives, anti-oxidants, emulsifying agents, buffers, colorants, flavors, nucleotides, and nucleosides, additional probiotics, additional prebiotics, lactoferrin, and related derivatives, thickening agents and stabilizers, and so forth.

Product Form

The preterm infant formulas of the present disclosure may be prepared as any product form suitable for use in humans, including liquid or powdered complete nutritionals, liquid or powdered supplements (such as a supplement that can be mixed with a drink), reconstitutable powders, ready-to-feed liquids, bars, and dilutable liquid concentrates, which product forms are all well known in the nutritional formula arts.

The preterm infant formulas of the present disclosure may have any caloric density suitable for the targeted or intended patient population, i.e., preterm infants, or provide such a density upon reconstitution of a powder embodiment or upon dilution of a liquid concentrate embodiment. Most common caloric densities for the formulas of the present disclosure are generally at least about 19 kcal/fl oz (660 kcal/liter), more typically from about 20 kcal/fl oz (675-680 kcal/liter) to about 31 kcal/fl oz, even more typically from about 20 kcal/fl oz (675-680 kcal/liter) to about 24 kcal/fl oz (800-810 kcal/liter). Generally, 22-24 kcal/fl oz formulas are more commonly used in preterm or low birth weight infants, and the 20-21 kcal/fl oz (675-680 to 700 kcal/liter) formulas are more often used in term infants.

For nutritional powder embodiments of the present disclosure, such powders are typically in the form of flowable or substantially flowable particulate compositions, or at least particulate compositions that can be easily scooped and measured with a spoon or similar other device, wherein the compositions can easily be reconstituted by the intended user with a suitable aqueous fluid, typically water, to form a liquid nutritional formula for immediate oral or enteral use. In this context, "immediate" use generally means within about 48 hours, most typically within about 24 hours, preferably right after reconstitution. These powder embodiments include spray dried, agglomerated, dry mixed or other known or otherwise effective particulate form. The quantity of a nutritional powder required to produce a volume suitable for one serving may vary.

The preterm infant formulas of the present disclosure may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

Methods of Manufacture

The preterm infant formulas of the present disclosure may be prepared by any known or otherwise effective technique suitable for making and formulating a nutritional formula or similar other formula, variations of which may depend upon variables such as the selected product form, ingredient combination, packaging and container selection, and so forth, for the desired preterm infant formula. Such techniques and variations for any given formula are easily determined and applied by one of ordinary skill in the nutritional formulation or manufacturing arts.

The preterm infant formulas of the present disclosure, including the exemplified formulas described hereinafter, can therefore be prepared by any of a variety of known or otherwise effective formulation or manufacturing methods. These methods most typically involve the initial formation of an aqueous slurry containing carbohydrates, proteins, lipids, stabilizers or other formulation aids, vitamins, minerals, or combinations thereof. The slurry is emulsified, pasteurized, homogenized, and cooled. Various other solutions, mixtures, or other materials may be added to the resulting emulsion before, during, or after further processing. This emulsion can then be further diluted, heat-treated, and packaged to form a ready-to-feed or concentrated liquid, or it can be heat-treated and subsequently processed and packaged as a reconstitutable powder, e.g., spray dried, dry mixed, agglomerated.

Other suitable methods for making nutritional formulas are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application No. 20030118703 A1 (Nguyen, et al.), which descriptions are incorporated herein by reference.

Methods of Use

The preterm infant formulas of the present disclosure can be administered to any individual as a nutrition source, e.g., in the form of a nutritional formula, especially to infants, or more particularly to preterm infants.

The preterm infant formulas of the present disclosure may also be used for the purpose of modulating levels of C-reactive protein (CRP), and thus inflammation, in an individual, and particularly in preterm infants. Specifically, CRP has gained recognition as a marker for inflammatory conditions. In humans, CRP levels are elevated in response to infection, trauma, surgery, and tissue infarction. Preterm infants often have increased inflammation and oxidative stress associated with common diseases of prematurity, such as chronic lung disease, bronchopulmonary dysplasia (BPD), retinopathy of prematurity (ROP), necrotizing enterocolitis (NEC), and intraventricular hemorrhage (IVH), among others. The skin of preterm infants is also immature and susceptible to inflammation. These common issues associated with prematurity may result in elevated levels of CRP in preterm infants.

It has now been discovered that administering a preterm infant formula containing the levels of beta-carotene, lutein, and lycopene set forth herein, to a preterm infant allows the levels of CRP in the preterm infants to be modulated. More specifically, the formulas of the present disclosure, when administered to a preterm infant, can decrease plasma concentrations of CRP in the preterm infant. Since CRP is a well known marker for inflammatory conditions, by decreasing plasma concentrations of CRP in the preterm infant, the level of inflammation can also be modulated (i.e., decreased).

Thus, in one aspect, the present disclosure is directed to a method for modulating inflammation in preterm infants. The method comprises administering to the preterm infant an effective amount of a preterm infant formula of the present disclosure. The modulation of inflammation may be, for example, a reduction in inflammation, preferably skin inflammation, such as is measured by a decrease in the plasma concentration of CRP in the preterm infant. Plasma concentration of CRP can be measured with a standard CRP test of the blood.

In another aspect, the present disclosure is directed to a method for modulating levels of CRP in a preterm infant. The method comprises administering to the preterm infant an effective amount of a preterm infant formula of the present disclosure. The modulation of CRP levels may be, for example, a decrease in the plasma concentration of CRP in the preterm infant. Preferably, the administration of the preterm infant formula also results in an increase in the levels of beta-carotene, lutein, and lycopene in the skin of the preterm infant.

An "effective amount" of the preterm infant formula is any amount effective to achieve the desired reduction in inflammation and/or CRP levels in the preterm infant. Typically, the preterm infant formula is administered to a preterm infant in amounts of from about 100 mL/day to about 1000 mL/day, more typically in amounts of from about 150 mL/day to about 700 mL/day. Preferably, the preterm infant formula is administered in sufficient amounts to provide from about 22 µg/kg/day to about 150 µg/kg/day of lutein; from about 18 µg/kg/day to about 150 µg/kg/day of lycopene; and from about 26 µg/kg/day to about 150 µg/kg/day of beta-carotene In preterm infants, the formula may be administered at any time during which it is desirable to modulate inflammation and/or CRP levels in preterm infants. Typically, the formula is administered from start of enteral feeding until typically up to about 50 weeks post-menstrual age, or up to about 40 weeks post-menstrual age. Preferably, the preterm infant formula is administered at least until the plasma concentration of CRP in the preterm infant has decreased and/or until the levels of beta-carotene, lutein, and/or lycopene in the skin are increased.

EXAMPLES

The following examples further describe and demonstrate specific embodiments within the scope of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

Each of the exemplified formulas is fed to humans to provide sole, primary, or supplemental nutrition. Each formula contains carotenoids as described herein, and can be used to modulate inflammation and/or levels of C-reactive protein in preterm infants.

Examples 1-15

The following examples illustrate preterm infant formulas of the present disclosure, including methods of making and using the preterm infant formulas. Formula ingredients for each batch are listed in Table 2. Exemplary amounts of beta-carotene, lutein, and lycopene provided by each formula when prepared as a ready-to-feed (RTF) formula, which may be varied depending on the amount of water used to prepare the RTF formula, is set forth in Tables 3 and 4.

TABLE 2

Preterm Infant Formulas Comprising Carotenoids

| Ingredients | Example 1 Quantity per 1000 kg | Example 2 Quantity per 1000 kg | Example 3 Quantity per 1000 kg |
| --- | --- | --- | --- |
| Water (kg) | 681.6 | 747 | 795 |
| Non Fat Dry Milk (kg) | 180.7 | 127.3 | 98.0 |
| Corn syrup (kg) | 38.39 | 38.8 | 35.19 |
| Corn syrup solids (kg) | 36.47 | 36.9 | 33.43 |
| Medium chain triglycerides (kg) | 31.60 | 20.8 | 15.42 |
| Soy oil (kg) | 18.96 | 12.4 | 9.25 |
| Whey Protein Concentrate (kg) | 14.11 | 16.6 | 12.69 |

TABLE 2-continued

Preterm Infant Formulas Comprising Carotenoids

| Ingredients | Example 1 Quantity per 1000 kg | Example 2 Quantity per 1000 kg | Example 3 Quantity per 1000 kg |
|---|---|---|---|
| Coconut oil (kg) | 11.56 | 7.48 | 5.64 |
| Lactose (kg) | 7.13 | 16.3 | 17.23 |
| 5% KOH (kg) | 6.37 | 5.10 | 4.86 |
| Potassium hydroxide solids (kg) | 0.319 | 0.255 | 0.243 |
| Ultra-micronized tricalcium phosphate (kg) | 2.81 | 2.41 | 2.56 |
| Ascorbic acid (kg) | 1.14 | 0.913 | 0.888 |
| Vitamin/Mineral/Taurine Premix (g) | 802.7 | 642 | 537 |
| Calcium Carbonate (g) | 680 | 476 | 98 |
| Soy lecithin (g) | 659 | 433 | 364 |
| Monoglycerides (g) | 659 | 433 | 364 |
| Magnesium chloride (g) | 554 | 424 | 404 |
| ARASCO *M. alpine* oil (g) | 541 | 433 | 364 |
| Sodium citrate (g) | 438.5 | 203 | As needed |
| Nucleotide/Choline Premix (g) | 366.5 | 293 | 293 |
| DHASCO *C. cohnii* oil (g) | 339.0 | 272 | 229 |
| Carotenoid premixed suspension | | | |
| Beta-carotene (mg) | 100 | 226 | 280 |
| Lutein (mg) | 100 | 218 | 250 |
| Lycopene (mg) | 100 | 147 | 180 |
| Vitamin A, D3, E, K1 (g) | 123.6 | 98.9 | 82.39 |
| Seakem RLC carrageenan (g) | 120.0 | 150 | 299 |
| Seakem GP-359 carrageenan (g) | — | 150 | — |
| Ferrous Sulfate (g) | 72.97 | 58.4 | 48.83 |
| Choline Chloride (g) | 60.07 | 48.1 | 35.42 |
| L-carnitine (g) | 40.34 | 36.6 | 30.62 |
| Potassium citrate (2) (g) | 4.60 | — | 3.080 |
| Thiamine HCl (g) | 4.34 | — | — |
| Riboflavin (g) | 1.8 | — | — |
| Vitamin A (g) | 0.463 | 1.25 | 1.606 |
| Vitamin A palmitate (g) | 0.254 | 0.685 | 0.880 |
| Potassium citrate (1) | As needed | 261 | 335 |
| Sodium Chloride | — | As needed | As needed |
| Potassium Chloride (g) | As needed | 196 | 140 |
| Potassium phosphate | As needed | As needed | As needed |

TABLE 3

Carotenoid Concentration in RTF Formula

| Carotenoid | Example 4 | Example 5 | Example 6 | Example 7 | Example 8 | Example 9 |
|---|---|---|---|---|---|---|
| Beta-carotene (μg/L) | 85 | 144 | 203 | 219 | 262 | 321 |
| Lutein (μg/L) | 75 | 90 | 158 | 211 | 251 | 294 |
| Lycopene (μg/L) | 60 | 78 | 129 | 143 | 198 | 257 |

TABLE 4

Carotenoid Concentration in RTF Formula

| Carotenoid | Example 10 | Example 11 | Example 12 | Example 13 | Example 14 | Example 15 |
|---|---|---|---|---|---|---|
| Beta-carotene (μg/L) | 380 | 439 | 500 | 180 | 295 | 260 |
| Lutein (μg/L) | 362 | 430 | 500 | 120 | 265 | 202 |
| Lycopene (μg/L) | 319 | 417 | 500 | 100 | 219 | 188 |

The exemplified formulas may be prepared as a powdered nutritional infant formula by making at least two separate slurries that are later blended together, heat treated, standardized, heat treated a second time, spray dried, agglomerated, dry blended, and packaged, or may be prepared as a liquid ready-to-feed infant nutritional formula by making at least two separate slurries that are later blended together, heat treated, standardized, diluted with an appropriate amount of water, packaged, and sterilized. Initially, a carbohydrate-mineral slurry is prepared by dissolving the carbohydrates in water at 60-71° C., followed by the addition of magnesium chloride, choline chloride, sodium chloride, potassium chloride, and calcium carbonate. The resulting slurry is held under moderate agitation at 49-60° C. until it is later blended with the other prepared slurries.

An oil slurry is prepared by combining the medium chain triglycerides, monoglycerides, soy oil, coconut oil, arachidonic acid, and docosahexaenoic acid (DHA) at 49-60° C., followed by the addition of carotenoids (beta-carotene, lutein, lycopene), Vitamin A, vitamin ADEK premix, and lecithin. The resulting oil slurry is held under moderate agitation at 38-49° C. until it is later blended with the other prepared slurries.

A protein slurry is prepared by dissolving non-fat dry milk and whey protein concentrate in water at approximately 5-30° C. The resulting protein slurry is held under low agitation at 2-7° C. until it is later blended with the other prepared slurries.

Water, the carbohydrate-mineral slurry, and the protein slurry are combined under adequate agitation. The oil slurry is then added. The pH of the resulting blend is adjusted with potassium hydroxide. This blend is held under moderate agitation at 49-60° C.

The resulting blend is heated to 71-77° C., emulsified to a maximum of 300 psig, and then homogenized at 2400-2600/400-600 psig. The blend is then heated to 144-146° C. for about 5 seconds. The heated blend is then cooled to a temperature of about 4° C. Samples are taken for microbiological and analytical testing. The mixture is held under agitation.

A vitamin/mineral/taurine premix solution and an ascorbic acid solution are prepared separately and added to the processed blended slurry. The vitamin/mineral/taurine premix solution is prepared by adding the following ingredients to water with agitation: potassium citrate, sodium citrate, potassium phosphate, ultra-micronized tricalcium phosphate, ferrous sulfate, vitamin/mineral/taurine premix, L-carnitine, and the nucleotide-choline premix. The ascorbic acid solution is prepared by adding potassium hydroxide and ascorbic acid to a sufficient amount of water to dissolve the ingredients. The ascorbic acid solution pH is then adjusted to 5-9 with potassium hydroxide.

To prepare a powdered nutritional infant formula, the blend pH may be adjusted with potassium hydroxide to achieve optimal product stability. The blend then receives a second heat treatment. The blend is originally heated to 71-77° C., and then further heated to 144-146° C. for about 5 seconds. The heated blend is then passed through a flash cooler to reduce the temperature to 71-82° C. Following heat treatment, the blend is evaporated.

The evaporated blend is passed through a spray drier. The finished powder then undergoes agglomeration with water as the binder solution. The probiotic is dryblended into the product. The completed product is then packaged into suitable containers.

To prepare a ready-to-feed nutritional infant formula, based on the analytical results of the quality control tests, an appropriate amount of water is added to the batch with agitation to achieve the desired total solids. The product pH may be adjusted to achieve optimal product stability. The completed product is then placed in suitable containers and subjected to terminal sterilization.

The resulting formula is then used to provide a supplemental, primary, or sole source of nutrition to premature infants or other appropriate individuals.

Example 16

A study was conducted to evaluate and compare the plasma concentrations of beta-carotene, lutein, and lycopene in preterm infants fed a regimen of preterm infant formulas with mixed carotenoids to plasma concentrations in preterm infants fed a regimen of preterm infant formulas with no added carotenoids, and to a reference group of human milk (HM)-fed preterm infants. Skin carotenoid concentrations in preterm infants fed preterm infant formulas with mixed carotenoids were also compared to those in the preterm infants fed preterm infant formulas with no added carotenoids and to the reference group of HM-fed preterm infants.

The study was a randomized, controlled, double-blinded, parallel study. Two-hundred three preterm infants from birth to 21 days of age were enrolled. Formula fed infants were administered an in-hospital formula (Similac® Special Care® formula (SSC)) with (study formula) or without (control formula) added carotenoids from start of enteral feeding until 40 weeks post-menstrual age (PMA), unless the infant reached 3.5 kg of body weight earlier or until the in-hospital, higher caloric formula was no longer medically indicated. At that time, infants were switched to the corresponding post-discharge formula (Similac® NeoSure® formula), with (study formula) or without (control formula) added carotenoids, and were administered the post-discharge formula until 50 weeks PMA (10 weeks corrected age). Infants remained on the same feeding regimen throughout the study. Specifically, infants administered the in-hospital formula with added carotenoids were switched to the post-discharge formula with added carotenoids, while infants fed the in-hospital formula without added carotenoids were switched to the post-discharge formula without the added carotenoids. The compositions of the formulas used in this study are set forth in Table 5.

TABLE 5

Composition of Control and Study Formulas

| Nutrient | In-hospital RTF formulas (24 kcal/oz) | | Post-discharge RTF formulas (22 kcal/oz) | |
| --- | --- | --- | --- | --- |
| | SSC | SSC with added carotenoids | NeoSure® | NeoSure® with added carotenoids |
| Protein, g | 24.4 | 24.4 | 20.8 | 20.8 |
| Source | Nonfat milk, whey protein conc. | Nonfat milk, whey protein conc. | Nonfat milk, whey protein conc. | Nonfat milk, whey protein conc. |
| Fat, g | 44.0 | 44.0 | 40.9 | 40.9 |
| Source | MCT, soy, coconut, *M. alpina*, *C. cohnii* oils | MCT, soy, coconut, *M. alpina*, *C. cohnii* oils | soy, coconut, MCT, *M. alpina*, *C. cohnii* oils | soy, coconut, MCT, *M. alpina*, *C. cohnii* oils |
| Oil Ratio | (50:30:18.3) | (50:30:18.3) | (44.7:29:24.9) | (44.7:29:24.9) |
| % fatty acids | 0.40% ARA, 0.25% DHA | 0.40% ARA, 0.25% DHA | 0.40% ARA, 0.25% DHA | 0.40% ARA, 0.25% DHA |
| Carbohydrate, g | 83.6 | 83.6 | 75.1 | 75.1 |
| Minerals | | | | |
| Calcium, mg | 1461 | 1461 | 781 | 781 |
| Phosphorus, mg | 812 | 812 | 464 | 464 |
| Ca:P ratio | 1.7 | 1.7 | 1.7 | 1.7 |
| Magnesium, mg | 97.4 | 97.4 | 67.0 | 67.0 |
| Sodium, mg | 349 | 349 | 245 | 245 |
| Potassium, mg | 1047 | 1047 | 1056 | 1056 |
| Chloride, mg | 657 | 657 | 558 | 558 |
| Iron, mg | 14.6 | 14.6 | 13.4 | 13.4 |
| Zinc, mg | 12.1 | 12.1 | 9.0 | 9.0 |
| Copper, mg | 2.0 | 2.0 | 0.9 | 0.9 |
| Manganese, µg | 97 | 97 | 74 | 74 |
| Selenium, µg | 14.6 | 14.6 | 15.7 | 15.7 |
| Vitamins | | | | |
| A, IU | 10144 | 10144 | 3422 | 3422 |
| Thiamin, mg | 2.03 | 2.03 | 1.6 | 1.6 |
| Riboflavin, mg | 5.0 | 5.0 | 1.1 | 1.1 |
| $B_6$, mg | 2.6 | 2.6 | 0.8 | 0.8 |
| $B_{12}$, µg | 4.5 | 4.5 | 3.0 | 3.0 |
| Biotin, µg | 350 | 350 | 80 | 80 |
| Pantothenic acid, mg | 15.4 | 15.4 | 6.0 | 6.0 |
| Folic acid, µg | 540 | 540 | 200 | 200 |

TABLE 5-continued

Composition of Control and Study Formulas

| Nutrient | In-hospital RTF formulas (24 kcal/oz) | | Post-discharge RTF formulas (22 kcal/oz) | |
|---|---|---|---|---|
| | SSC | SSC with added carotenoids | NeoSure ® | NeoSure ® with added carotenoids |
| C, mg | 300 | 300 | 112 | 112 |
| D, IU | 1217 | 1217 | 521 | 521 |
| E, IU | 32.5 | 32.5 | 26.8 | 26.8 |
| K, μg | 97.4 | 97.4 | 81.8 | 81.8 |
| Taurine, mg | 60 | 60 | 50 | 50 |
| Carnitine, mg | 12 | 12 | 44 | 44 |
| Inositol, mg | 45 | 45 | 45 | 45 |
| Choline, mg | 18 | 18 | 119 | 119 |
| Carotenoids* | | | | |
| Beta-carotene, μg/L | 20† | 220 | 28† | 90 |
| Lutein, μg/L | NA | 212 | NA | 90 |
| Lycopene, μg/L | NA | 143 | NA | 59 |

†Inherent levels of beta-carotene in the control product
NA Concentrations were not measured
*Average of five batches The formula fed infants were randomized to receive control or study formula. Human milk fed infants were also randomized. If for some reason human milk became insufficient or the mother chose not to human milk feed her baby at any time during the study, the feedings were supplemented with the formula randomly assigned at enrollment (i.e., the control or study formula). If formula (i.e., the randomly assigned control or study formula) accounted for 60% or more of the total volume of enteral intake in-hospital, the originally assigned human milk fed infant was evaluated with the appropriate formula subjects.

Of the 203 randomized subjects, 143 completed the study. Of these subjects who completed the study, 108 completed the study on the assigned feeding. Subjects were considered to have completed the study if they followed the assigned study feeding until 50 weeks PMA.

The lutein, lycopene, and beta-carotene intake, calculated from the actual amount of formula consumed by the subject, for subjects receiving the formulas with added carotenoids (i.e., study formulas) is set forth in Table 6.

Blood samples (1.5 mL in-hospital and 0.5 mL post-discharge) were taken from the subjects at study day 1, at hospital discharge, at 40 weeks PMA, and at 50 weeks PMA. Blood samples were sent to Craft Technologies (Wilson, N.C.) for determination of plasma concentrations of lutein, lycoene, beta-carotene, and C-reactive protein. The plasma concentrations of lutein, lycopene, and beta-carotene in evaluable subjects at study day 1, at hospital discharge, and at 40 and 50 weeks PMA are shown in Tables 7-10. The plasma concentrations of C-reactive protein at study day 1, at hospital discharge, and at 40 and 50 weeks PMA are shown in Table 11. Growth, including weight gain, length gain, and head circumference, of the infants (study formula group, control formula group, and milk-fed group) was also determined in hospital and at 40 and 50 weeks PMA. Growth was not different between the control formula group and the study formula group at any time during the study, if human milk intake was controlled for in the analyses (data not shown).

Tables 7-11 set forth results for subjects classified as "evaluable." The evaluable analysis for a defined study out-

TABLE 6

Carotenoid Intake (μg/kg/day) for Evaluable Subjects Fed Study Formulas

| | Visit | | | |
|---|---|---|---|---|
| | In Hospital | 40 wks PMA | 44 wks PMA | 50 wks PMA |
| Total lutein intake (μg/kg/day) | | | | |
| Mean ± SEM | 23.7 ± 0.9 | 32.3 ± 3.8 | 14.7 ± 1.1 | 13.1 ± 0.6 |
| Range | 8.2-35.3 | 6.7-103.2 | 8.8-41.8 | 7.9-21.2 |
| N | 46 | 31 | 31 | 29 |
| Total lycopene intake (μg/kg/day) | | | | |
| Mean ± SEM | 16.1 ± 0.6 | 22.0 ± 2.5 | 10.6 ± 0.8 | 9.4 ± 0.4 |
| Range | 5.7-23.9 | 4.8-69.8 | 6.3-30.1 | 5.7-15.3 |
| N | 46 | 31 | 31 | 29 |
| Total beta-carotene intake (μg/kg/day) | | | | |
| Mean ± SEM | 24.6 ± 1.0 | 33.7 ± 3.9 | 16.1 ± 1.2 | 14.3 ± 0.7 |
| Range | 8.7-36.6 | 7.3-106.9 | 9.7-45.8 | 8.6-23.3 |
| N | 46 | 31 | 31 | 29 | come included data collected from a subject following the feeding protocol at the time of observation of the outcome. A subject's outcome data were classified as 'evaluable' for the analysis until one or more of the exclusion events occurred during the study. Exclusion events included correct randomization but incorrect dispensing of assigned formula, refusal or unsuccessful blood draws, volume of formula intake accounting for less than 60% of total volume in-hospital, and days of formula intake accounting for less than 60% of study interval after hospital discharge. In addition, a subject was removed from the evaluable analysis if the subject received less than 7 days of study formula in-hospital, subject was NPO (i.e., nothing taken by mouth) all day for at least 10 days in-hospital, or at 50 weeks, subject exited study more than 7 days after last study formula was received. These criteria were established to ensure that infants were exposed to an acceptable amount of the assigned formula (control or study) during the in-hospital phase and post-discharge phase of the study.

TABLE 7

Plasma Concentrations of Lutein** (μg/dL) in Evaluable Subjects

| Lutein (μg/dL) | Study Group | | HM Reference Groups | |
| --- | --- | --- | --- | --- |
| | Control Formula (CF) | Study Formula (SF) | Preterm | Term* |
| Study Day 1[†] | | | | |
| Mean ± SEM | 1.71 ± 0.14 | 2.41 ± 0.19 | 2.44 ± 0.13 | |
| Median | 1.40 | 2.10 | 2.30 | |
| Range | 0.30-4.40 | 0.60-5.40 | 0.70-4.80 | |
| N | 42 | 37 | 52 | |
| Hospital discharge[‡] | | | | |
| Mean ± SEM | 0.82 ± 0.08 | 6.96 ± 0.84 | 2.73 ± 0.44 | |
| Median | 0.80 | 6.90 | 2.70 | |
| Range | 0.20-2.30 | 0.70-21.20 | 0.30-8.40 | |
| N | 31 | 30 | 23 | |
| 40 wks PMA[‡] | | | | |
| Mean ± SEM | 0.92 ± 0.08 | 10.30 ± 0.95 | 3.83 ± 0.54 | |
| Median | 0.90 | 10.90 | 3.00 | |
| Range | 0.20-2.60 | 0.70-24.60 | 0.20-15.90 | |
| N | 43 | 36 | 39 | |
| 50 wks PMA[‡] | | | | |
| Mean ± SEM | 1.83 ± 0.40 | 7.68 ± 0.58 | 3.94 ± 0.60 | 5.88 ± 0.77 |
| Median | 1.40 | 7.60 | 3.10 | 4.72 |
| Range | 0.20-11.80 | 0.80-15.50 | 0.20-13.10 | 0.49-20.09 |
| N | 28 | 26 | 35 | 26 |

Abbreviations used: HM = human milk; PMA = post-menstrual age
*Human milk reference group data adapted from Mackey, et al., "Relative bioavailability of carotenoids in infant formula and human milk," presented at Clinical Nutrition Week, Chicago, February 2008. Plasma lutein concentration values were obtained at 10-13 weeks of age from term infants fed HM.
**Plasma concentrations for lutein include concentrations of the trans isomer.
[†]SF > CF; p < 0.01.
[‡]SF > CF; p < 0.0001.

TABLE 8

Plasma Concentration of Lycopene** (μg/dL) in Evaluable Subjects

| Total Lycopene (μg/dL) | Study Group | | HM Reference Groups | |
| --- | --- | --- | --- | --- |
| | Control Formula (CF) | Study Formula (SF) | Preterm | Term* |
| Study day 1 | | | | |
| Mean ± SEM | 1.07 ± 0.12 | 1.33 ± 0.15 | 1.43 ± 0.15 | |
| Median | 0.90 | 1.30 | 1.10 | |
| Range | 0.30-3.40 | 0.10-4.80 | 0.30-5.10 | |
| N | 42 | 37 | 52 | |
| Hospital discharge[†] | | | | |
| Mean ± SEM | 0.33 ± 0.01 | 4.41 0 ± 0.65 | 1.42 ± 0.23 | |
| Median | 0.30 | 3.70 | 1.20 | |
| Range | 0.30-0.60 | 0.30-15.90 | 0.30-3.60 | |
| N | 31 | 30 | 23 | |
| 40 wks PMA[†] | | | | |
| Mean ± SEM | 0.31 ± 0.01 | 7.93 ± 0.86 | 2.17 ± 0.32 | |
| Median | 0.30 | 7.30 | 1.50 | |
| Range | 0.30-0.60 | 0.30-21.50 | 0.30-10.10 | |
| N | 43 | 36 | 39 | |

TABLE 8-continued

Plasma Concentration of Lycopene** (μg/dL) in Evaluable Subjects

| Total Lycopene (μg/dL) | Study Group | | HM Reference Groups | |
| --- | --- | --- | --- | --- |
| | Control Formula (CF) | Study Formula (SF) | Preterm | Term* |
| 50 wks PMA† | | | | |
| Mean ± SEM | 0.32 ± 0.01 | 10.78 ± 0.91 | 3.25 ± 0.62 | 10.85 ± 1.08 |
| Median | 0.30 | 10.70 | 1.90 | 11.21 |
| Range | 0.30-0.60 | 0.30-21.00 | 0.30-11.20 | 0.3-23.13 |
| N | 28 | 26 | 35 | 26 |

Abbreviations used: HM = human milk; PMA = post-menstrual age
*Human milk reference group data adapted from Mackey, et al., "Relative bioavailability of carotenoids in infant formula and human milk," presented at Clinical Nutrition Week, Chicago, February 2008. Plasma lycopene concentration values were obtained at 10-13 weeks of age from term infants fed HM.
**Plasma concentrations of lycopene include concentrations of the cis and trans isomers.
†SF > CF; p < 0.0001.

TABLE 9

Plasma Concentrations of Beta-Carotene** (μg/dL) in Evaluable Subjects

| Total Beta-Carotene (μg/dL) | Study Group | | HM Reference Groups | |
| --- | --- | --- | --- | --- |
| | Control Formula (CF) | Study Formula (SF) | Preterm | Term* |
| Study day 1 | | | | |
| Mean ± SEM | 0.97 ± 0.14 | 1.21 ± 0.25 | 1.46 ± 0.22 | |
| Median | 0.55 | 0.70 | 0.90 | |
| Range | 0.30-4.10 | 0.30-8.20 | 0.30-7.40 | |
| N | 42 | 37 | 52 | |
| Hospital discharge† | | | | |
| Mean ± SEM | 0.74 ± 0.14 | 4.79 ± 0.64 | 3.42 ± 0.90 | |
| Median | 0.40 | 4.15 | 2.20 | |
| Range | 0.30-3.60 | 0.30-13.40 | 0.30-14.80 | |
| N | 31 | 30 | 23 | |
| 40 wks PMA† | | | | |
| Mean ± SEM | 0.83 ± 0.09 | 7.22 ± 0.74 | 4.81 ± 0.98 | |
| Median | 0.80 | 6.85 | 1.60 | |
| Range | 0.30-3.60 | 0.50-16.10 | 0.30-24.30 | |
| N | 43 | 36 | 39 | |
| 50 wks PMA† | | | | |
| Mean ± SEM | 4.52 ± 1.43 | 8.49 ± 1.26 | 9.37 ± 2.04 | 6.79 ± 1.51 |
| Median | 1.25 | 6.55 | 4.70 | 3.65 |
| Range | 0.50-34.80 | 3.60-35.40 | 0.30-48.00 | 0.40-29.89 |
| N | 28 | 26 | 35 | 26 |

Abbreviations used: HM = human milk; PMA = post-menstrual age
*Human milk reference group data adapted from Mackey, et al., "Relative bioavailability of carotenoids in infant formula and human milk," presented at Clinical Nutrition Week, Chicago, February 2008. Plasma beta-carotene concentration values were obtained at 10-13 weeks of age from term infants fed HM.
**Plasma concentrations of beta-carotene include concentrations of the cis and trans isomers.
†SF > CF; p < 0.0001.

TABLE 10

Plasma Concentrations of Total Lutein/Zeaxanthin* (μg/dL) in Evaluable Subjects

| Total Lutein/Zeaxanthin (μg/dL) | Treatment group including HM | | |
| --- | --- | --- | --- |
| | Control Formula (CF) | Study Formula (SF) | HM |
| Study day 1 | | | |
| Mean ± SEM | 2.65 ± 0.22 | 3.74 ± 0.31 | 3.69 ± 0.18 |
| Median | 2.25 | 3.40 | 3.45 |
| Min, Max | 0.40, 6.90 | 0.70, 8.40 | 1.10, 6.60 |
| N | 42 | 37 | 52 |
| Hosp. disc. | | | |
| Mean ± SEM | 1.11 ± 0.10 | 8.45 ± 0.99 | 4.13 ± 0.65 |
| Median | 1.10 | 7.90 | 4.80 |
| Min, Max | 0.20, 2.70 | 0.90, 25.40 | 0.50, 12.60 |
| N | 31 | 30 | 23 |

TABLE 10-continued

Plasma Concentrations of Total Lutein/Zeaxanthin*
(μg/dL) in Evaluable Subjects

| Total Lutein/Zeaxanthin (μg/dL) | Treatment group including HM | | |
|---|---|---|---|
| | Control Formula (CF) | Study Formula (SF) | HM |
| 40 wks PMA | | | |
| Mean ± SEM | 1.15 ± 0.10 | 12.35 ± 1.12 | 5.69 ± 0.76 |
| Median | 1.10 | 12.80 | 4.60 |
| Min, Max | 0.20, 3.40 | 1.00, 29.80 | 0.20, 23.20 |
| N | 43 | 36 | 39 |
| 50 wks PMA | | | |
| Mean ± SEM | 2.46 ± 0.44 | 9.25 ± 0.75 | 5.65 ± 0.84 |
| Median | 1.95 | 9.30 | 4.50 |
| Min, Max | 0.20, 13.00 | 0.90, 19.30 | 0.20, 16.30 |
| N | 28 | 26 | 35 |

Abbreviations used: HM = Human Milk; PMA = Post-menstrual age
Statistical analysis was not done on plasma concentrations of total lutein/zeaxanthin.
*Plasma concentrations of total lutein/zeaxanthin include concentrations of cis and trans isomers of lutein. The cis isomer of lutein can not be separated from the cis isomer of zeaxanthin. Plasma concentrations of total lutein/zeaxanthin were not included in the primary analyses but are shown because infants in the study formula group did receive some zeaxanthin during the study.

As can be seen from Tables 7-10, plasma lycopene and beta-carotene concentrations were not different at enrollment (study day 1), but plasma lutein concentrations were different between the study groups (SF>CF; p<0.01) at study day 1. At hospital discharge, plasma concentrations of lutein, lycopene, and beta-carotene were significantly higher in the study formula group (added carotenoids), compared to the control formula group (no added carotenoids). Infants in the study formula group had significantly higher mean plasma concentration of lutein than infants in the control group (6.96 vs. 0.82 μg/dL; p<0.0001) at hospital discharge. Similarly, mean plasma lycopene concentration was significantly higher in the study formula group than in the control formula group (4.41 vs. 0.33 μg/dL; p<0.0001) at hospital discharge. Mean plasma beta-carotene concentration was also significantly higher in the study formula group than in the control formula group (4.79 vs. 0.74 μg/dL; p<0.0001).

The mean plasma lutein concentrations at 40 and 50 weeks PMA were also significantly higher in the study formula (SF) group compared to the control formula (CF) group in evaluable subjects (10.30 μg/dL>0.93 μg/dL, p<0.0001; 7.68 μg/dL>1.83 μg/dL, p<0.0001, respectively). The plasma lutein concentration in the study formula group was thus closer to the plasma lutein levels reported in term human milk fed infants (i.e., mean of 5.88 μg/dL; range of 0.49-20.09 μg/dL) at approximately 10-13 weeks of age than was the plasma concentrations of the control formula group.

Plasma lycopene and beta-carotene concentrations were significantly higher (p<0.0001) in the study formula group as compared to the control formula group at 40 weeks and 50 weeks PMA for evaluable subjects. Specifically, the mean plasma lycopene levels in the study formula group were 7.93 μg/dL and 10.78 μg/dL at 40 and 50 weeks PMA, respectively. In contrast, the mean lycopene plasma concentrations in the control formula group were only 0.31 μg/dL and 0.32 μg/dL (considered undetectable) at 40 and 50 weeks PMA, respectively. The plasma lycopene concentration in the study formula group was thus closer to the plasma lycopene levels reported in term human milk fed infants (i.e., mean of 10.85 μg/dL; range of 0.3-23.13 μg/dL) at approximately 10-13 weeks of age, than was the plasma concentrations of the control formula group.

The mean plasma beta-carotene levels in the study formula group were 7.22 μg/dL and 8.49 μg/dL at 40 and 50 weeks PMA, respectively, for evaluable subjects. In contrast, the mean beta-carotene plasma concentrations in the control formula group were 0.83 μg/dL and 4.52 μg/dL at 40 and 50 weeks PMA. The plasma beta-carotene concentration in the study formula group was thus closer to the plasma lycopene levels reported in term human milk fed infants (i.e., mean of 6.79 μg/dL; range of 0.40-29.89 μg/dL) at approximately 10-13 weeks of age, than was the plasma concentration of the control formula group.

The plasma concentrations of C-reactive protein (CRP) at study day 1, at hospital discharge, and at 40 and 50 weeks PMA in evaluable subjects that received the study formula (with added carotenoids) are shown in Table 11.

TABLE 11

Plasma Concentrations of C-Reactive
Protein (μg/mL) in Evaluable Subjects

| C-reactive protein (μg/mL) | Study Group | | |
|---|---|---|---|
| | Control Formula (CF) | Study Formula (SF) | HM * |
| Study Day 1 | | | |
| Mean ± SEM | 0.763 ± 0.167 | 0.853 ± 0.225 | 0.773 ± 0.319 |
| Median | 0.385 | 0.410 | 0.260 |
| Range | 0.020-5.570 | 0.020-7.320 | 0.020-16.550 |
| N | 42 | 37 | 52 |
| Hospital discharge | | | |
| Mean ± SEM | 0.827 ± 0.355 | 0.343 ± 0.079 | 0.343 ± 0.113 |
| Median | 0.400 | 0.200 | 0.120 |
| Range | 0.020-10.340 | 0.020-1.910 | 0.020-2.160 |
| N | 29 | 27 | 23 |
| 40 wks PMA † | | | |
| Mean ± SEM | 3.250 ± 1.017 | 0.536 ± 0.130 | 1.826 ± 0.610 |
| Median | 0.600 | 0.180 | 0.210 |
| Range | 0.020-26.580 | 0.020-3.240 | 0.020-17.400 |
| N | 38 | 36 | 38 |
| 50 wks PMA | | | |
| Mean ± SEM | 1.644 ± 0.723 | 2.822 ± 0.927 | 0.423 ± 0.110 |
| Median | 0.220 | 0.360 | 0.290 |
| Range | 0.020-16.190 | 0.020-19.270 | 0.020-3.600 |
| N | 27 | 25 | 35 |

Abbreviations used: HM = human milk.
* HM reference group only. These data were not included in the statistical analyses
† CF > SF; p < 0.001.

As can be seen from Table 11, CRP levels at 40 weeks PMA were significantly lower in the study formula group as compared to the control formula group (p<0.001). FIG. 1 is a graph showing the median CRP levels from study day 1 to 40 weeks PMA for the control formula group, study formula group, and the human milk fed reference group. As can be seen from FIG. 1, CRP levels decreased in the study formula group and the human milk fed group whereas they increased in the control formula group from study day 1 to 40 weeks PMA.

The results of the CRP evaluation suggest that carotenoids may play a role in modulating inflammation in preterm infants, and that this may be related to the amount of carotenoids administered to the infant. Specifically, the time period during which CRP levels decreased in the study formula group relative to control (i.e., study day 1 to 40 weeks PMA) is the time period during which the study formula infants were receiving the in-hospital formula study formula. As can be seen from Table 5 above, the in-hospital study formula (Similac® Special Care® formula with added carotenoids) contained higher concentrations of carotenoids than the post-discharge study formula (Neosure® formula with added carotenoids). The total carotenoid intake at 40 weeks PMA (i.e., at the time the study group infants were receiving the Similac® Special Care® study formula) was at least two times higher than the total carotenoid intake at 50 weeks PMA (i.e., at the time the study group infants were receiving the NeoSure® study formula) (see Table 6).

The plasma concentration of CRP for evaluable infants in the study formula group (see Table 11) was plotted verses the plasma concentration of lutein, lycopene, and beta-carotene. The results are shown in FIGS. 2-4. As can be seen from FIGS. 2-4, the plasma concentration of CRP decreases with increasing plasma concentrations of lutein (FIG. 2), lycopene (FIG. 3), and beta-carotene (FIG. 4), indicating that the plasma concentrations of lutein, lycopene, and beta-carotene are separately inversely related to the plasma concentrations of CRP.

CONCLUSION

There were consistent differences between the study formula and the control formula groups in regards to plasma concentrations of lutein, lycopene and beta-carotene. Specifically, plasma concentrations of lutein, lycopene and beta-carotene were consistently higher in the study formula group as compared to the control formula group at hospital discharge, and at 40 and 50 weeks PMA. The concentration of carotenoids in the plasma of the study formula group was closer to that observed in human milk fed term infants, than was the plasma concentration of the control group subjects. Infants in both the study formula and control formula groups had good growth, indicating that both formulas provided adequate nutrition to the infants and were well tolerated.

Plasma concentration of CRP at 40 weeks PMA was significantly lower in the study formula group as compared to the control formula group, but was not significantly different at 50 weeks PMA, suggesting that carotenoids may play a role in modulating inflammation. Since the total carotenoid intake at 40 weeks PMA (i.e., at the time the study group infants were receiving the Similac® Special Care® study formula supplemented with high levels of carotenoids) was at least two times higher than the total carotenoid intake at 50 weeks PMA (i.e., at the time the study group infants were receiving the NeoSure® study formula supplemented with lower levels of carotenoids), the role of carotenoids in modulating inflammation may be related to the amount of carotenoids administered to the infant.

The results also demonstrated that plasma concentrations of the carotenoids beta-carotene, lutein, and lycopene are inversely correlated with plasma concentrations of CRP. Plasma carotenoid levels were also significantly correlated with skin carotenoid levels, as determined by Raman spectroscopy (data not shown).

What is claimed is:

1. A method of modulating inflammation in an infant having inflammation characterized by an elevated plasma level of C-reactive protein, the method comprising:
    administering to the infant having inflammation characterized by an elevated plasma level of C-reactive protein a preterm infant formula comprising about 75 μg/L to about 500 μg/L of lutein, about 60 μg/L to about 500 μg/L of lycopene, and about 85 μg/L to about 500 μg/L of beta-carotene.

2. The method of claim 1, wherein the inflammation characterized by an elevated plasma level of C-reactive protein is due to infection.

3. The method of claim 1, wherein the inflammation is decreased by decreasing the plasma level of C-reactive protein in the infant.

4. The method of claim 1, wherein the preterm infant formula is administered to the infant until the plasma level of C-reactive protein in the infant has decreased.

5. The method of claim 1, wherein the inflammation characterized by an elevated plasma level of C-reactive protein is skin inflammation.

6. The method of claim 1, wherein the infant is a preterm infant, and the preterm infant formula is administered to the preterm infant until the preterm infant reaches about 40 weeks post-menstrual age.

7. The method of claim 1, wherein the infant is a preterm infant, and the preterm infant formula is administered to the preterm infant until the preterm infant reaches about 50 weeks post-menstrual age.

8. The method of claim 1, wherein the preterm infant formula comprises about 200 μg/L to about 250 μg/L of lutein, about 100 μg/L to about 150 μg/L of lycopene, and about 200 μg/L to about 250 μg/L of beta-carotene.

9. The method of claim 8, wherein the preterm infant formula comprises about 212 μg/L of lutein, about 143 μg/L of lycopene, and about 220 μg/L of beta-carotene.

10. The method of claim 1, wherein the preterm infant formula provides to the infant about 22 μg/kg/day to about 150 μg/kg/day of lutein, about 18 μg/kg/day to about 150 μg/kg/day of lycopene, and about 26 μg/kg/day to about 150 μg/kg/day of beta-carotene.

11. The method of claim 1, wherein the preterm infant formula further comprises about 5 μg/L to about 50 μg/L of zeaxanthin.

12. The method of claim 1, wherein the preterm infant formula further comprises at least one of vitamins, minerals, carbohydrate, lipid, and protein.

13. The method of claim 1, wherein the preterm infant formula comprises, as a percentage of total calories, about 35% to about 50% carbohydrate, about 30% to about 60% lipid, and about 7.5% to about 25% protein.

14. A method of modulating the plasma level of C-reactive protein in an infant having an elevated plasma level of C-reactive protein, the method comprising:
    administering to the infant having an elevated plasma level of C-reactive protein a preterm infant formula comprising about 75 μg/L to about 500 μg/L of lutein, about 60 μg/L to about 500 μg/L of lycopene, and about 85 μg/L to about 500 μg/L of beta-carotene.

15. The method of claim 14, wherein the elevated plasma level of C-reactive protein is due to infection.

16. The method of claim 14, wherein the infant is a preterm infant, and the preterm infant formula is administered to the preterm infant until the preterm infant reaches about 40 weeks post-menstrual age.

17. The method of claim 14, wherein the infant is a preterm infant, and the preterm infant formula is administered to the preterm infant until the preterm infant reaches about 50 weeks post-menstrual age.

18. The method of claim 14, wherein the preterm infant formula comprises about 200 μg/L to about 250 μg/L of lutein, about 100 μg/L to about 150 μg/L of lycopene, and about 200 μg/L to about 250 μg/L of beta-carotene.

19. The method of claim 18, wherein the preterm infant formula comprises about 212 μg/L of lutein, about 143 μg/L of lycopene, and about 220 μg/L of beta-carotene.

20. The method of claim 14, wherein the preterm infant formula provides to the infant about 22 μg/kg/day to about 150 μg/kg/day of lutein, about 18 μg/kg/day to about 150 μg/kg/day of lycopene, and about 26 μg/kg/day to about 150 μg/kg/day of beta-carotene.

21. The method of claim 14, wherein the preterm infant formula further comprises about 5 μg/L to about 50 μg/L of zeaxanthin.

\* \* \* \* \*